(12) United States Patent
Jeon et al.

(10) Patent No.: US 9,194,782 B2
(45) Date of Patent: Nov. 24, 2015

(54) VACUUM THERMAL-INSULATION MATERIAL, AND A DEVICE AND METHOD FOR ASSESSING THE DEGREE OF VACUUM IN THE VACUUM INSULATION MATERIAL BY USING THE FREQUENCY RESPONSE METHOD

(75) Inventors: Seung-Min Jeon, Busan (KR); Sung-Seock Hwang, Cheongju-si (KR); Jung-Pil Han, Ulsan (KR)

(73) Assignee: LG HAUSYS, LTD., Seoul (KR)

( * ) Notice: Subject to any disclaimer, the term of this patent is extended or adjusted under 35 U.S.C. 154(b) by 254 days.

(21) Appl. No.: 13/876,411

(22) PCT Filed: Sep. 21, 2011

(86) PCT No.: PCT/KR2011/006960
§ 371 (c)(1),
(2), (4) Date: Mar. 27, 2013

(87) PCT Pub. No.: WO2012/044003
PCT Pub. Date: Apr. 5, 2012

(65) Prior Publication Data
US 2013/0192335 A1    Aug. 1, 2013

(30) Foreign Application Priority Data

Sep. 29, 2010    (KR) .................... 10-2010-0094448

(51) Int. Cl.
*G01N 3/30*    (2006.01)
*F16L 59/065*    (2006.01)
*G01M 7/08*    (2006.01)

(52) U.S. Cl.
CPC ............... *G01N 3/30* (2013.01); *F16L 59/065* (2013.01); *G01M 7/08* (2013.01); *Y10T 428/231* (2015.01)

(58) Field of Classification Search
CPC .......... F16L 59/065; G01N 3/30; G01M 7/08; Y10T 428/231
USPC ....................... 73/12.01, 12.09, 11.01; 428/69
See application file for complete search history.

(56) References Cited

U.S. PATENT DOCUMENTS 4,479,386 A * 10/1984 Beggs et al. ..................... 73/582
4,502,329 A * 3/1985 Fukunaga et al. ............... 73/573
5,885,682 A    3/1999 Tanimoto et al.
(Continued)

FOREIGN PATENT DOCUMENTS

CN    101292111 A    10/2008
JP    08159377 A    6/1996
(Continued)

OTHER PUBLICATIONS

Chinese Office Action dated Jul. 2, 2014.
(Continued)

*Primary Examiner* — Lisa Caputo
*Assistant Examiner* — Philip Cotey
(74) *Attorney, Agent, or Firm* — Hauptman Ham, LLP

(57) ABSTRACT

Disclosed herein is a vacuum insulation material, which includes a barrier film and a core, wherein a rigid body thinner than a reference thickness or a getter harder than a reference hardness is formed between the barrier film and the core, or the rigid body thinner than the reference thickness is formed on the getter formed between the barrier film and the core to ensure surface flatness and surface hardness of the vacuum insulation material.

13 Claims, 3 Drawing Sheets

(56) References Cited

U.S. PATENT DOCUMENTS

| | | | |
|---|---|---|---|
| 2002/0168496 A1* | 11/2002 | Morimoto et al. | 428/69 |
| 2003/0082357 A1* | 5/2003 | Gokay et al. | 428/212 |
| 2005/0005571 A1* | 1/2005 | Manini et al. | 52/741.1 |
| 2007/0196665 A1* | 8/2007 | Tenra et al. | 428/416 |
| 2008/0280090 A1* | 11/2008 | Kim et al. | 428/69 |
| 2008/0286515 A1 | 11/2008 | Jung et al. | |
| 2009/0031659 A1* | 2/2009 | Kalfon | 52/404.1 |
| 2011/0037482 A1* | 2/2011 | Oh et al. | 324/551 |
| 2013/0192335 A1* | 8/2013 | Jeon et al. | 73/12.01 |

FOREIGN PATENT DOCUMENTS

| | | |
|---|---|---|
| JP | 08-219751 | 8/1996 |
| JP | 2001-021336 | 1/2001 |
| JP | 2007040391 A | 2/2007 |
| JP | 2010071303 A | 4/2010 |
| KR | 10-1996-0021511 | 7/1996 |
| KR | 10-0690895 | 3/2007 |

OTHER PUBLICATIONS

Japanese Office Action dated Sep. 16, 2014.
Japanese Notice of Allowance dated Jan. 6, 2015.
International Search Report mailed Apr. 26, 2012 for PCT/KR2011/006960.

* cited by examiner

VACUUM THERMAL-INSULATION MATERIAL, AND A DEVICE AND METHOD FOR ASSESSING THE DEGREE OF VACUUM IN THE VACUUM INSULATION MATERIAL BY USING THE FREQUENCY RESPONSE METHOD

TECHNICAL FIELD

The present invention relates to a vacuum insulation material, and a method and apparatus for evaluating an internal vacuum degree of a vacuum insulation material based on frequency response.

BACKGROUND ART

A vacuum insulation material includes a porous filler (core) and a barrier (barrier film) surrounding the filler, and has very low thermal conductivity by removing gas from the barrier film to maintain a vacuum for several years or more.

Insulation performance of the vacuum insulation material depends on the degree of vacuum therein and decreases as the internal vacuum degree is lowered. Thus, it is important to identify a defect of a product through evaluation of the internal vacuum degree of the vacuum insulation material.

In the related art, however, the degree of vacuum is evaluated based on thermal resistance obtained by converting heat flux and potential values on the surface of the vacuum insulation material.

Reliability of a vacuum evaluation method in the related art can vary according to sensitivity of a sensor for detecting heat flux and potential values and measurement conditions. In addition, in the vacuum evaluation method in the related art, since the degree of vacuum in the vacuum insulation material can be evaluated only in relation with thermal resistance instead of being directly evaluated, it is necessary to impart strong stress to the surface of the vacuum insulation material for a long period of time.

DISCLOSURE

Technical Problem

Some embodiments of the present invention provide a vacuum insulation material which may disperse or mitigate impact according to surface flatness and surface hardness of the vacuum insulation material when the impact is applied to the surface of the vacuum insulation material.

Other embodiments of the present invention provide an apparatus for evaluating an internal vacuum degree of a vacuum insulation material, which applies impact force to a surface of the vacuum insulation material and then measure a natural frequency of the vacuum insulation material to evaluate the internal vacuum degree of the vacuum insulation material using a relationship between the degree of vacuum in the vacuum insulation material and the natural frequency, and a method of evaluating an internal vacuum degree of a vacuum insulation material using the same.

Some embodiments of the present invention provide an apparatus for evaluating an internal vacuum degree of a vacuum insulation material, which does not require application of strong stress to the surface of the vacuum insulation material and a long period of time for evaluation, and can evaluate the internal vacuum degree based only on rigidity of the vacuum insulation material according to the internal vacuum degree, thereby enabling useful application of the vacuum insulation material to quality inspection, and a method of evaluating an internal vacuum degree of a vacuum insulation material using the same.

The present invention is not limited to the above embodiments, and other embodiments will become apparent by those skilled in the art.

Technical Solution

One aspect of the present invention provides a vacuum insulation material including: a barrier film; and a core, wherein a rigid body thinner than a reference thickness or a getter harder than a reference hardness is formed between the barrier film and the core, or the rigid body thinner than the reference thickness is formed on the getter formed between the barrier film and the core to ensure surface flatness and surface hardness of the vacuum insulation material.

The reference thickness may range from 0.5 mm to 0.5 mm.

The reference hardness may range from 2H to 4H.

Another aspect of the present invention provides an apparatus for evaluating an internal vacuum degree of a vacuum insulation material, including: a hammer unit which applies impact to a portion of a surface of the vacuum insulation material corresponding to a rigid body or a getter in the vacuum insulation material to excite the vacuum insulation material; a displacement measuring unit which measures displacement of a material point according to the impact applied to the vacuum insulation material; a frequency analysis unit which measures a natural frequency of the vacuum insulation material based on the measured displacement; and a vacuum evaluation unit which evaluates the internal vacuum degree of the vacuum insulation material based on the natural frequency.

The frequency analysis unit may process the measured displacement via Fourier Transform to obtain a frequency spectrum and analyze the frequency spectrum to measure the natural frequency of the vacuum insulation material.

The vacuum evaluation unit may compare the natural frequency measured by the frequency analysis unit with the reference frequency to evaluate the internal vacuum degree of the vacuum insulation material.

The reference frequency may be an average value of natural frequencies of normal vacuum insulation materials for specific sizes and weights and may be within a predetermined reference frequency range.

When the measured natural frequency deviates from the reference frequency range, the vacuum evaluation unit may determine that the internal vacuum degree of the vacuum insulation material is poor, and when the measured natural frequency is within the reference frequency range, the vacuum evaluation unit may determine that the internal vacuum degree of the vacuum insulation material is good.

The apparatus may further include: a force sensor for measuring a magnitude of force transferred to the vacuum insulation material as the hammer unit strikes the vacuum insulation material. The frequency analysis unit may convert the measured displacement to a mechanical compliance value according to an equation regarding a relationship between the displacement and the force, and analyze the converted mechanical compliance value in a frequency region to measure the natural frequency of the vacuum insulation material.

The displacement measuring unit may include a laser displacement sensor which measures displacement while being separated a predetermined distance from the vacuum insulation material.

A further aspect of the present invention provides an apparatus for evaluating an internal vacuum degree of a vacuum insulation material, which includes: a hammer unit which applies impact to a portion of a surface of the vacuum insulation material corresponding to a rigid body or a getter in the vacuum insulation material; an acceleration measuring unit which measures acceleration of a material point according to the impact applied to the vacuum insulation material; a frequency analysis unit which measures a natural frequency of the vacuum insulation material based on the measured acceleration; and a vacuum evaluation unit which evaluates the internal vacuum degree of the vacuum insulation material based on the natural frequency.

The frequency analysis unit may process the measured acceleration via Fourier Transform to obtain a frequency spectrum and analyze the frequency spectrum to measure the natural frequency of the vacuum insulation material.

The acceleration measuring unit may include a laser acceleration sensor which measures the acceleration while being separated a predetermined distance from the vacuum insulation material.

Yet another aspect of the present invention provides a method of evaluating an internal vacuum degree of a vacuum insulation material, which includes: applying impact to a portion of a surface of the vacuum insulation material corresponding to a rigid body or a getter in the vacuum insulation material; measuring displacement of a material point according to the impact applied to the vacuum insulation material; measuring a natural frequency of the vacuum insulation material based on the measured displacement; and evaluating an internal vacuum degree of the vacuum insulation material based on the natural frequency.

The measuring a natural frequency of the vacuum insulation material may include: processing the measured displacement via Fourier Transform to obtain a frequency spectrum; and analyzing the frequency spectrum to measure the natural frequency of the vacuum insulation material.

The evaluating an internal vacuum degree of the vacuum insulation material may include: determining that the internal vacuum degree of the vacuum insulation material is poor when the measured natural frequency deviates from a reference frequency range; and determining that the internal vacuum degree of the vacuum insulation material is good when the measured natural frequency is within the reference frequency range.

The method may further include: measuring a magnitude of force transferred to the vacuum insulation material as the hammer unit strikes the vacuum insulation material; converting the measured displacement to a mechanical compliance value according to an equation regarding a relationship between the displacement and the force; and analyzing the converted mechanical compliance value in a frequency region to measure the natural frequency of the vacuum insulation material.

The measuring displacement of a material point may include measuring the displacement of the material point using a laser displacement sensor separated a predetermined distance from the vacuum insulation material.

Yet another aspect of the present invention provides a method of evaluating an internal vacuum degree of a vacuum insulation material, which includes: applying impact to a portion of a surface of the vacuum insulation material corresponding to a rigid body or a getter in the vacuum insulation material; measuring acceleration of a material point according to the impact applied to the vacuum insulation material; measuring a natural frequency of the vacuum insulation material based on the measured acceleration; and evaluating an internal vacuum degree of the vacuum insulation material based on the natural frequency.

The measuring a natural frequency of the vacuum insulation material may include: processing the measured acceleration by via Fourier Transform to obtain a frequency spectrum; and analyzing the frequency spectrum to measure the natural frequency of the vacuum insulation material.

The measuring acceleration of a material point may include measuring the acceleration of the material point using a laser acceleration sensor separated a predetermined distance from the vacuum insulation material.

Yet another aspect of the present invention provides a method of evaluating an internal vacuum degree of a vacuum insulation material, which includes: applying impact to a portion of a surface of the vacuum insulation material, which corresponds to a rigid body or a getter in the vacuum insulation material, with an exciter for generating force; measuring acceleration of a material point according to the impact applied to the vacuum insulation material; measuring a natural frequency of the vacuum insulation material based on the measured acceleration; and evaluating an internal vacuum degree of the vacuum insulation material based on the natural frequency.

The measuring a natural frequency of the vacuum insulation material may include: processing the measured acceleration via Fourier Transform to obtain a frequency spectrum; and analyzing the frequency spectrum to measure the natural frequency of the vacuum insulation material.

The measuring acceleration of a material point may include measuring the acceleration of the material point using a laser acceleration sensor separated a predetermined distance from the vacuum insulation material.

Details of other embodiments will be described in the following description with reference to the accompanying drawings.

The above and other aspects, features, and advantages of the present invention will become apparent from the detailed description of the following embodiments in conjunction with the accompanying drawings. It should be understood that the present invention is not limited to the following embodiments and may be embodied in different ways, and that the embodiments are given to provide complete disclosure and a thorough understanding of the present invention to those skilled in the art. The scope of the present invention is defined only by the claims. The same components will be denoted by the same reference numerals throughout the specification.

Advantageous Effects

According to some embodiments of the present invention, the vacuum insulation material may disperse or mitigate impact according to surface flatness and surface hardness of the vacuum insulation material when the impact is applied to the surface of the vacuum insulation material.

According to other embodiments of the present invention, the method and apparatus for evaluating an internal vacuum degree of a vacuum insulation material may apply impact to a surface of the vacuum insulation material and measure a natural frequency of the vacuum insulation material to evaluate the internal vacuum degree of the vacuum insulation material using a relationship between the degree of vacuum in the vacuum insulation material and the natural frequency.

According to some embodiments of the present invention, the method and apparatus for evaluating an internal vacuum degree of a vacuum insulation material do not require application of strong stress to the surface of the vacuum insulation material and a long period of time for evaluation, and can evaluate the internal vacuum degree based only on rigidity of the vacuum insulation material according to the internal vacuum degree, thereby enabling useful application of the vacuum insulation material to quality inspection.

BEST MODE

Figure 1:
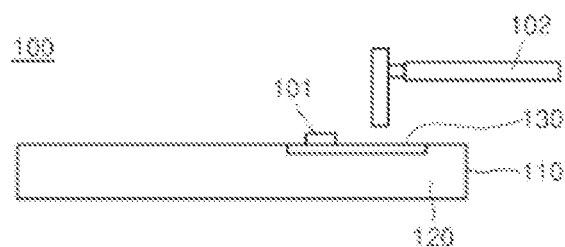
FIG. 1 is a side view of a vacuum insulation material according to one embodiment of the present invention.

Embodiments of the present invention provide apparatuses for evaluating an internal vacuum degree of a vacuum insulation material, which may measure impact and displacement or acceleration of a material point upon application of the impact to a surface of the vacuum insulation material and may analyze a natural frequency of the vacuum insulation material to evaluate an internal vacuum degree of the vacuum insulation material.

The vacuum insulation material is converted from an atmospheric state into a vacuum state when air in a core is exhausted as an internal vacuum degree thereof increases or an inner pressure thereof is lowered, and thus stiffness of the vacuum insulation material increases as the core is contracted. In particular, a barrier film is firmly bonded to the core due to pressure difference between the interior and the exterior of the vacuum insulation material with respect to the middle of the barrier film.

However, when the vacuum state in the vacuum insulation material is released, the stiffness of the vacuum insulation material is lowered due to introduction of air into the core and flexibility increases through restoration of the core to its original state. In particular, an air layer is formed between the core and the barrier film, so that the stiffness of the vacuum insulation material is lowered while increasing a damping value thereof.

Thus, displacement of a material point by impact is converted into a mechanical compliance (displacement/force) value, which is analyzed in a frequency region to obtain a natural frequency of the vacuum insulation material, and the internal vacuum degree of the vacuum insulation material can be evaluated through analysis of the natural frequency.

When the natural frequency is analyzed through frequency analysis, the natural frequency changes as damping ratio increases due to release of the vacuum in the vacuum insulation material. Here, it is assumed that the film (barrier film) and the core of the vacuum insulation material is formed as a single body (single mass) due to the internal vacuum pressure of the vacuum insulation material.

In this way, in some embodiments, it can be seen that the natural frequency changes as the damping coefficient increases due to release of the vacuum in the vacuum insulation material, and the degree of vacuum in the vacuum insulation material can be evaluated.

In some embodiments, when applied to a surface of the vacuum insulation material, impact can be dispersed and reduced according to flatness and hardness of the surface of the vacuum insulation material. Thus, in some embodiments, a thin rigid body made of, for example, steel or aluminum, is inserted into the vacuum insulation material and impact is applied to the corresponding portion.

However, a protrusion may be created on the surface of the vacuum insulation material due to the thin rigid body. Thus, in some embodiments, a getter is made hard or a thin rigid body is located at an upper end of the getter to minimize the thickness of the protrusion on the surface of the vacuum insulation material.

Further, in some embodiments, displacement or acceleration is measured using a displacement sensor or an acceleration sensor. In this case, a laser sensor capable of measuring displacement or acceleration at a predetermined distance from a target is more advantageous than a piezoelectric sensor attached to the surface of the vacuum insulation material.

However, in some embodiments, when the piezoelectric sensor is attached to the surface of the vacuum insulation material to be used, it is more advantageous in measuring the displacement or the acceleration to attach the piezoelectric sensor to a portion of the surface of the vacuum insulation material having good flatness.

In some embodiments, an internal vacuum degree of the vacuum insulation material may be evaluated by measuring natural frequencies of normal vacuum insulation material products according to size and weight thereof and setting a frequency region obtained through a window to an average natural frequency.

Now, embodiments of the present invention will be described in detail with reference to the accompanying drawings.

FIG. 1 is a view of a vacuum insulation material according to one embodiment of the present invention.

In FIG. 1, a vacuum insulation material 100 according to this embodiment includes a barrier film 110, a core 120, and a rigid body 130.

When applied to a surface of the general vacuum insulation material 100 by an impact hammer 102, impact may be dispersed or mitigated according to the flatness and hardness of the surface of the vacuum insulation material 100.

Thus, in this embodiment, the thin rigid body 130 formed of steel or aluminum is advantageously inserted into the vacuum insulation material 100 between the barrier film 110 and the core 120. According to the present embodiment, an internal vacuum degree of the vacuum insulation material 100 may be evaluated by applying impact to a portion of the surface of the vacuum insulation material 100 into which the rigid body 130 is inserted, and measuring displacement or acceleration through a displacement sensor or an acceleration sensor 101.

Here, the rigid body 130 has a smaller thickness than a reference thickness, which may range from 0.5 mm to 1.5 mm. If the rigid body 130 is thicker than the reference thickness, the rigid body 130 protrudes from the surface of the vacuum insulation material 100, so that the vacuum insulation material 100 has an uneven surface, thereby causing a bonding problem and the like.

Figure 2:
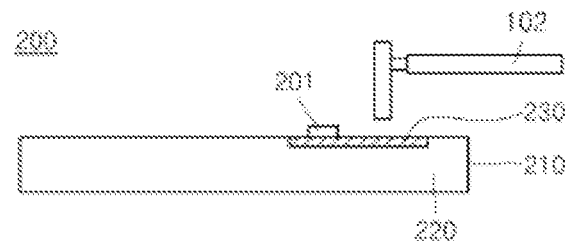
FIG. 2 is a side view of a vacuum insulation material according to another embodiment of the present invention.

FIG. 2 is a view of a vacuum insulation material according to another embodiment of the present invention.

In FIG. 2, a vacuum insulation material 200 according to this embodiment includes a barrier film 210, a core 220, and a getter 230.

As in FIG. 1, the rigid body 130 is inserted between the barrier film 110 and the core 120. At this time, a protrusion can be formed on the surface of the vacuum insulation material 100 when the rigid body 130 is thicker than the reference value.

Thus, in the present embodiment, the getter 230 may be hard and inserted between the barrier film 210 and the core 220 instead of the rigid body 130 of FIG. 1. Accordingly, according to this embodiment, a protruding thickness on the surface of the vacuum insulation material 200 protrudes may be minimized.

Here, the getter 230 is harder than a reference hardness, which may range from 2H to 4H. The getter 230 is harder than the reference hardness in order to allow impact to be dispersed or mitigated by a damping effect of the getter 230 upon application of the impact to a portion of the surface of the vacuum insulation material 200 into which the getter 230 is inserted.

Figure 3:
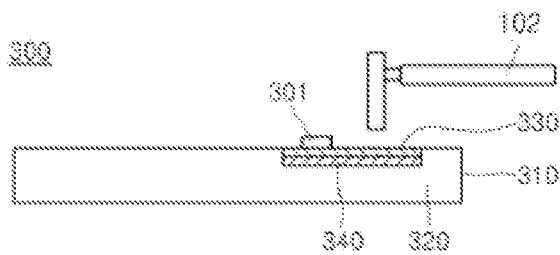
FIG. 3 is a side view of a vacuum insulation material according to a further embodiment of the present invention.

FIG. 3 is a view of a vacuum insulation material according to a further embodiment of the present invention.

In FIG. 3, a vacuum insulation material 300 according to this embodiment includes a barrier film 310, a core 320, a rigid body 330, and a getter 340.

As described above, in FIG. 1, the rigid body 130 is inserted between the barrier film 110 and the core 120, and if the rigid body 130 is thicker than a reference thickness, a protrusion can be created on the surface of the vacuum insulation material 100.

Thus, in the present embodiment, the rigid body 330 and the getter 340 are inserted between the barrier film 210 and the core 220, in which the getter 340 is hard and the thin rigid body 330 is located on the getter 340. According to this embodiment, a protruding thickness on the surface of the vacuum insulation material 300 protrudes may be minimized In this embodiment, the rigid body 330 has a smaller thickness than the reference thickness, which may range from 0.5 mm to 1.5 mm. If the rigid body 330 is thicker than the reference thickness, the rigid body 330 protrudes from the surface of the vacuum insulation material 300, so that the vacuum insulation material 300 has an uneven surface, thereby causing a bonding problem and the like.

Further, the getter 340 is harder than a reference hardness, which may range from 2H to 4H. The getter 340 is harder than the reference hardness in order to allow impact to be dispersed or mitigated by a damping effect of the getter 340 upon application of the impact to a portion of the surface of the vacuum insulation material 300 into which the getter 340 is inserted.

In this way, in the present embodiments, since at least one of the thin rigid body and the hard getter is inserted between the barrier film and the core of the vacuum insulation material, an internal vacuum degree of the vacuum insulation material may be more accurately evaluated.

Figure 4:
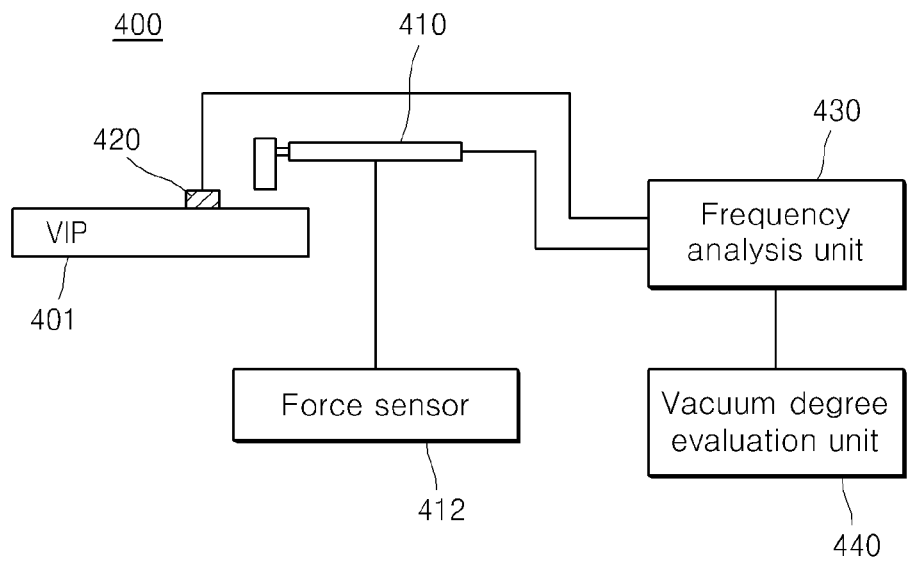
FIG. 4 is a diagram of an apparatus for evaluating an internal vacuum degree of a vacuum insulation material according to one embodiment of the present invention.

FIG. 4 is a diagram of an apparatus for evaluating an internal vacuum degree of a vacuum insulation material according to one embodiment of the present invention.

Referring to FIG. 4, the apparatus 400 according to the present embodiment includes a hammer unit 410, a displacement measuring unit 420, a frequency analysis unit 430, and a vacuum evaluation unit 440.

The hammer unit 410 is adapted to strike a vacuum insulation material 401 to apply impact to the vacuum insulation material 401.

The hammer unit 410 may apply impact to the vacuum insulation material 401 according to direct user manipulation. Alternatively, the hammer unit 410 may apply impact to the vacuum insulation material 401 while moving by operation of drive equipment.

Here, the drive equipment is provided to operate the hammer unit and is operated to apply a predetermined magnitude of force to the vacuum insulation material 401. Further, the drive equipment may be operated to apply various magnitudes of force to the vacuum insulation material 401.

A force sensor 412 may be received in the hammer unit 410. Alternatively, the force sensor 412 may be separately disposed from the hammer unit 410. In this way, various modifications may also be made.

The force sensor 412 serves to measure a magnitude of force transferred to the vacuum insulation material 401 as the hammer 410 strikes the vacuum insulation material 401. The magnitude of the force measured by the force sensor 412 is transferred to the frequency analysis unit 430, and the frequency analysis unit 430 may measure a natural frequency of the vacuum insulation material 401 based on the measured magnitude of the force.

The displacement measuring unit 420 measures displacement of a material point according to impact applied to the vacuum insulation material 401. That is, the displacement measuring unit 420 serves to measure displacement of a point (region) of the vacuum insulation material 401 to which the impact is applied.

As used herein, the term "material point" refers to an ideal point on which a mass of an object is regarded as being completely concentrated so that the object has only the mass without any physical volume.

The displacement measuring unit 420 may be realized by a laser displacement sensor which measures displacement while being separated a predetermined distance from the vacuum insulation material 401.

However, the displacement measuring unit 420 is not limited thereto, and various modifications may be made. For example, the displacement measuring unit 420 may be realized by a piezoelectric displacement sensor which measures a displacement while being attached to the vacuum insulation material 401.

The frequency analysis unit 430 measures the natural frequency of the vacuum insulation material 401 based on the measured displacement. That is, the frequency analysis unit 430 may process the measured displacement via FFT (Fast Fourier Transform) to obtain a frequency spectrum. The frequency analysis unit 430 may analyze the frequency spectrum to measure the natural frequency of the vacuum insulation material 401.

Meanwhile, as described above, the frequency analysis unit 430 may measure the natural frequency of the vacuum insulation material 401 based on the magnitude of the force measured by the force measuring sensor 412.

That is, the frequency analysis unit 430 may convert the measured displacement to a mechanical compliance value (displacement/force) according to an equation regarding a relationship between the displacement and the force. Further, the frequency analysis unit 430 may analyze the converted mechanical compliance value in a frequency region, and measure the natural frequency of the vacuum insulation material 401.

The vacuum evaluation unit 440 evaluates the internal vacuum degree of the vacuum insulation material 401 based on the measured natural frequency. To this end, the vacuum evaluation unit 440 may compare the natural frequency measured by the frequency analysis unit 430 with a reference frequency. The vacuum evaluation unit 440 may evaluate the internal vacuum degree of the vacuum insulation material 401 according to a comparison result.

Specifically, if the measured natural frequency deviates from a reference frequency range, the vacuum evaluation unit 440 may determine that the internal vacuum degree of the vacuum insulation material 401 is poor. On the contrary, if the measured natural frequency is within the reference frequency range, the vacuum evaluation unit 440 may determine that the internal vacuum degree of the vacuum insulation material 401 is good.

Here, the term "reference frequency" means a natural frequency of the normal vacuum insulation material 401. Normal vacuum insulation materials 401 may also have slightly different natural frequencies. Thus, the reference frequency may be preset to have a value within a predetermined range in consideration of such difference.

Meanwhile, an apparatus for evaluating an internal vacuum degree of a vacuum insulation material according to another embodiment of the present invention is similar to the vacuum degree evaluating apparatus 400 of FIG. 4. However, the apparatus according to this embodiment differs from the vacuum degree evaluating apparatus 400 in that the natural frequency of the vacuum insulation material is measured by measuring acceleration of a material point. Thus, in this embodiment, only an acceleration measuring unit will be described.

The acceleration measuring unit serves to measure acceleration of a material point upon application of impact to the vacuum insulation material. That is, the acceleration measuring unit measures acceleration of a point (region) of the vacuum insulation material to which impact is applied.

The acceleration measuring unit may be realized by a laser acceleration sensor which measures the acceleration while being separated a predetermined distance from the vacuum insulation material. However, the acceleration measuring unit is not limited thereto, and various modifications may be made. For example, the acceleration measuring unit may be realized by a piezoelectric displacement sensor which measures acceleration while being attached to the vacuum insulation material 401.

Figure 5:
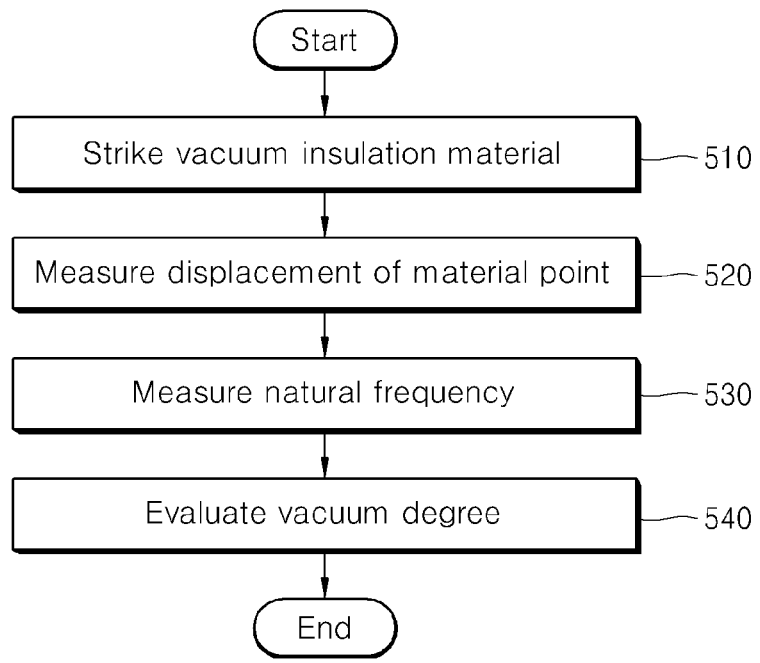
FIG. 5 is a flowchart of a method of evaluating an internal vacuum degree of a vacuum insulation material according to one embodiment of the present invention.

FIG. 5 is a flowchart of a method of evaluating an internal vacuum degree of a vacuum insulation material according to one embodiment of the present invention. Here, the method of evaluating an internal vacuum degree of a vacuum insulation material may be performed by the apparatus 400 for evaluating an internal vacuum degree of a vacuum insulation material as shown FIG. 4.

Referring to FIG. 5, in operation 510, the apparatus strikes a vacuum insulation material with a hammer to apply impact thereto. Here, the hammer may be automatically operated by a mechanical apparatus provided to the apparatus as described above, but may be manually operated by a user.

Next, in operation 520, the apparatus measures displacement of a material point according to the impact applied to the vacuum insulation material. That is, the apparatus serves to measure displacement of a point (region) of the vacuum insulation material to which the impact is applied.

Measurement of the displacement may be performed using a laser displacement sensor which measures the displacement while being separated a predetermined distance from the vacuum insulation material.

Next, in operation 530, the apparatus measures a natural frequency of the vacuum insulation material based on the measured displacement.

Namely, the apparatus may process the measured displacement via FFT (Fast Fourier Transform) to obtain a frequency spectrum.

Further, the apparatus may analyze the frequency spectrum to measure the natural frequency of the vacuum insulation material.

Meanwhile, the apparatus may measure the magnitude of force applied to the vacuum insulation material using a force sensor provided to the hammer. The apparatus may measure the natural frequency of the vacuum insulation material based on the magnitude of the force measured by the force sensor.

Specifically, the apparatus may convert the measured displacement to a mechanical compliance value (displacement/force) according to an equation regarding a relationship between the displacement and the force. Further, the apparatus may analyze the converted mechanical compliance value in a frequency region, and measure the natural frequency of the vacuum insulation material 401.

Next, in operation 540, the apparatus evaluates an internal vacuum degree of the vacuum insulation material based on the measured natural frequency. To this end, the apparatus may compare the natural frequency measured by the frequency analysis unit with a reference frequency. The vacuum evaluation unit may evaluate the internal vacuum degree of the vacuum insulation material according to a comparison result.

That is, if the measured natural frequency deviates from the reference frequency range, the apparatus may determine that the internal vacuum degree of the vacuum insulation material is poor. On the contrary, if the measured natural frequency is within the reference frequency range, the apparatus may determine that the internal vacuum degree of the vacuum insulation material is good.

Figure 6:
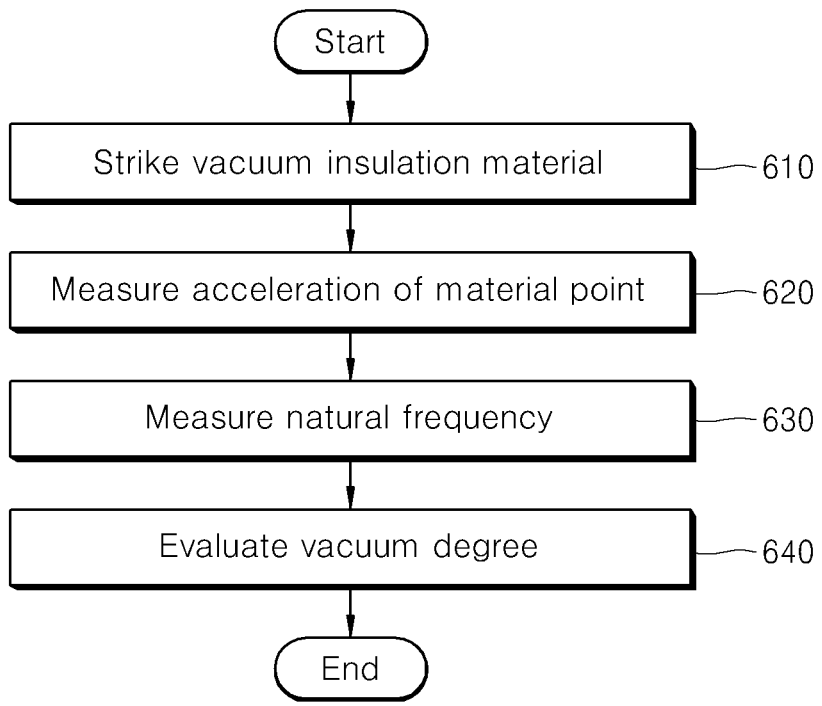
FIG. 6 is a flowchart of a method of evaluating an internal vacuum degree of a vacuum insulation material according to another embodiment of the present invention.

FIG. 6 is a flowchart of a method of evaluating an internal vacuum degree of a vacuum insulation material according to another embodiment of the present invention.

Referring to FIG. 6, in operation 610, the apparatus strikes a vacuum insulation material with a hammer to apply impact to the vacuum insulation material. Then, a vibrating exciter may be used as a tool for striking the vacuum insulation material in addition to the hammer.

Next, in operation 620, the apparatus measures acceleration of a material point according to the impact applied to the vacuum insulation material. That is, the apparatus serves to measure acceleration of a point (region) of the vacuum insulation material to which the impact is applied.

Here, measurement of the acceleration may be performed using a laser acceleration sensor which measures acceleration while being separated a predetermined distance from the vacuum insulation material.

Next, in operation 640, the apparatus measures a natural frequency of the vacuum insulation material based on the measured acceleration.

That is, the apparatus may process the measured acceleration via FFT (Fast Fourier Transform) to obtain a frequency spectrum.

Further, the apparatus may analyze the frequency spectrum to measure a natural frequency of the vacuum insulation material.

Next, in operation 640, the apparatus evaluates an internal vacuum degree of the vacuum insulation material based on the measured natural frequency. To this end, the apparatus may compare the measured natural frequency with a reference frequency. The apparatus may evaluate the internal vacuum degree of the vacuum insulation material according to a comparison result.

Specifically, if the measured natural frequency deviates from the reference frequency range, the apparatus may determine that the internal vacuum degree of the vacuum insulation material is poor. On the contrary, if the measured natural frequency is within the reference frequency range, the apparatus may determine that the internal vacuum degree of the vacuum insulation material is good.

As such, the embodiments of the present invention relate to a nondestructive evaluation method of vacuum insulation materials through frequency response, that is, a method of analyzing change in natural frequency according to an internal vacuum degree of a vacuum insulation material to evaluate the internal vacuum degree of the vacuum insulation material.

Thus, in the method and apparatus for evaluation of an internal vacuum degree of a vacuum insulation material according to the embodiments of present the invention, since application of strong stress to the surface of the vacuum insulation material and a long evaluation time are not required and the degree of vacuum may be evaluated based only on rigidity of the vacuum insulation material according to the internal vacuum degree thereof, the method and apparatus according to the embodiments of the present invention may be usefully applied to quality inspection of a vacuum insulation material.

Although some embodiments have been described herein, it should be understood that various modifications can be made without departing from the scope of the present invention.

Therefore, the scope of the present invention should not be limited to the embodiments described above, but should be determined according to the accompanied claims and equivalents thereof.

Although the present invention has been described with reference to the embodiments and the accompanying drawings, the present invention is not limited to the embodiments and various modifications and changes can be made by those skilled in the art.

Therefore, the spirit and scope of the present invention should be limited only by the following claims and equivalents thereof.

The invention claimed is:

1. A vacuum insulation material comprising:
   a barrier film; and
   a core, wherein a rigid body thinner than a reference thickness and a getter harder than a reference hardness are formed between the barrier film and the core, and the rigid body is formed on the getter to ensure surface flatness and surface hardness of the vacuum insulation material, wherein the reference thickness ranges from 0.5 mm to 1.5 mm, and reference hardness ranges from 2H to 4H.

2. An apparatus for evaluating an internal vacuum degree of a vacuum insulation material, comprising:
   a hammer unit which applies impact to a portion of a surface of the vacuum insulation material corresponding to a rigid body or a getter in the vacuum insulation material to excite the vacuum insulation material according to claim 1;
   a displacement measuring unit which measures displacement of a material point according to the impact applied to the vacuum insulation material;
   a frequency analysis unit which measures a natural frequency of the vacuum insulation material based on the measured displacement; and
   a vacuum evaluation unit which evaluates the internal vacuum degree of the vacuum insulation material based on the natural frequency.

3. The apparatus according to claim 2, wherein the frequency analysis unit processes the measured displacement via Fourier Transform to obtain a frequency spectrum and analyzes the frequency spectrum to measure the natural frequency of the vacuum insulation material.

4. The apparatus according to claim 2, wherein the vacuum evaluation unit compares the natural frequency measured by the frequency analysis unit with the reference frequency to evaluate the internal vacuum degree of the vacuum insulation material.

5. The apparatus according to claim 4, wherein the reference frequency is an average value of natural frequencies of normal vacuum insulation materials according to size and weight and is within a predetermined reference frequency range.

6. The apparatus according to claim 4, wherein, when the measured natural frequency deviates from the reference frequency range, the vacuum evaluation unit determines that the internal vacuum degree of the vacuum insulation material is poor, and when the measured natural frequency is within the reference frequency range, the vacuum evaluation unit determines that the internal vacuum degree of the vacuum insulation material is good.

7. The apparatus according to claim 2, further comprising:
   a force sensor for measuring a magnitude of force transferred to the vacuum insulation material as the hammer unit strikes the vacuum insulation material, wherein the frequency analysis unit converts the measured displacement to a mechanical compliance value according to an equation regarding a relationship between the displacement and the force, and analyzes the converted mechanical compliance value in a frequency region to measure the natural frequency of the vacuum insulation material.

8. The apparatus according to claim 2, wherein the displacement measuring unit comprises a laser displacement sensor which measures the displacement while being separated a predetermined distance from the vacuum insulation material.

9. A method of evaluating an internal vacuum degree of a vacuum insulation material, comprising:
   applying impact to a portion of a surface of the vacuum insulation material according to claim 1 corresponding to a rigid body or a getter in the vacuum insulation material;
   measuring displacement of a material point according to the impact applied to the vacuum insulation material;
   measuring a natural frequency of the vacuum insulation material based on the measured displacement; and
   evaluating an internal vacuum degree of the vacuum insulation material based on the natural frequency.

10. The method according to claim 9, wherein the measuring a natural frequency of the vacuum insulation material comprises:
    processing the measured displacement via Fourier Transform to obtain a frequency spectrum; and
    analyzing the frequency spectrum to measure the natural frequency of the vacuum insulation material.

11. The method according to claim 9, wherein the evaluating an internal vacuum degree of the vacuum insulation material comprises:
    determining that the internal vacuum degree of the vacuum insulation material is poor when the measured natural frequency deviates from a reference frequency range; and
    determining that the internal vacuum degree of the vacuum insulation material is good when the measured natural frequency is within the reference frequency range.

12. The method according to claim 9, further comprising:
    measuring a magnitude of force transferred to the vacuum insulation material as the hammer unit strikes the vacuum insulation material;

converting the measured displacement into a mechanical compliance value according to an equation regarding a relationship between the displacement and the force; and analyzing the converted mechanical compliance value in a frequency region to measure the natural frequency of the vacuum insulation material.

13. The method according to claim 9, wherein the measuring displacement of a material point comprises measuring the displacement of the material point using a laser displacement sensor separated a predetermined distance from the vacuum insulation material.

\* \* \* \* \*